(12) United States Patent
Funabiki et al.

(10) Patent No.: US 11,278,488 B2
(45) Date of Patent: Mar. 22, 2022

(54) COSMETIC

(71) Applicant: SUMITOMO SEIKA CHEMICALS CO., LTD., Hyogo (JP)

(72) Inventors: Yuhei Funabiki, Himeji (JP); Hirotsugu Kawata, Himeji (JP); Taiki Nishiyama, Osaka (JP); Toshiaki Fujiwara, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 0 days.

(21) Appl. No.: 16/098,223

(22) PCT Filed: Apr. 27, 2017

(86) PCT No.: PCT/JP2017/016821
§ 371 (c)(1),
(2) Date: Nov. 1, 2018

(87) PCT Pub. No.: WO2017/195642
PCT Pub. Date: Nov. 16, 2017

(65) Prior Publication Data
US 2019/0142730 A1 May 16, 2019

(30) Foreign Application Priority Data

May 10, 2016 (JP) .............................. JP2016-094714
Jun. 1, 2016 (JP) .............................. JP2016-109665
Jan. 23, 2017 (JP) .............................. JP2017-009675

(51) Int. Cl.
| | | |
|---|---|---|
| A61K 8/85 | (2006.01) | |
| A61Q 1/12 | (2006.01) | |
| A61Q 19/00 | (2006.01) | |
| A61K 8/02 | (2006.01) | |

(52) U.S. Cl.
CPC ............... *A61K 8/85* (2013.01); *A61K 8/022* (2013.01); *A61Q 1/12* (2013.01); *A61Q 19/00* (2013.01)

(58) Field of Classification Search
CPC . A61K 8/85; A61K 8/022; A61Q 1/12; A61Q 19/00
See application file for complete search history.

(56) References Cited

U.S. PATENT DOCUMENTS

| | | | |
|---|---|---|---|
| 8,802,814 B2 | 8/2014 | Le et al. | |
| 2004/0146540 A1* | 7/2004 | Ueda ..................... | A61K 8/025 424/401 |
| 2011/0287105 A1 | 11/2011 | Gittleman | |
| 2013/0309497 A1* | 11/2013 | Takezaki ................ | C08J 3/14 428/402 |
| 2013/0337025 A1* | 12/2013 | Le ........................... | C08G 63/91 424/401 |
| 2014/0017495 A1* | 1/2014 | Yamazaki ................. | C08J 3/12 428/402 |
| 2017/0247537 A1* | 8/2017 | Hipps, Sr. .................. | C08J 3/05 |

FOREIGN PATENT DOCUMENTS

| | | |
|---|---|---|
| EP | 1400233 A1 | 3/2004 |
| EP | 2660272 A1 | 11/2013 |
| JP | 5-194141 A | 8/1993 |
| JP | 5-262622 A | 10/1993 |
| JP | 2001-151626 A | 6/2001 |
| JP | 2002-370920 A | 12/2002 |
| JP | 2013-527204 A | 6/2013 |
| JP | 2014-503025 A | 2/2014 |
| JP | 2015-214690 A | 12/2015 |
| JP | 2017-88803 A | 5/2017 |
| WO | 2002/100357 A1 | 12/2002 |
| WO | 2011/149689 A1 | 12/2011 |
| WO | 2012/105140 A1 | 8/2012 |

OTHER PUBLICATIONS

MatWeb. "Overview of materials for Polylactic (PLA) Biopolymer". Retrieved on Oct. 21, 2019. Retrieved from the internet <URL: http://www.matweb.com/search/DataSheet.aspx?MatGUID=ab96a4c0655c4018a8785ac4031b9278&ckck=1>; pp. 1-4. (Year: 2019).*

Liminana et al. "Optimization of Maleinized Linseed Oil Loading as a Biobased Compatibilizer in Poly(Butylene Succicnate) Composites with Almond Shell Flour." Material, 2019, 12, 685, 1-14. (Year: 2019).*

Notification of Transmittal of Translation of the International Preliminary Report on Patentability (Form PCT/IB/338) issued in counterpart International Application No. PCT/JP2017/016821 dated Nov. 22, 2018, with Forms PCT/IB/373 and PCT/ISA/237. (15 pages).

International Search Report dated Jul. 18, 2017, issued in counterpart application No. PCT/JP2017/016821 (2 pages).

Extended European Search Report, dated Nov. 21, 2019, issued in counterpart European Application No. 17796003.6 (in English; 6 pages).

Office Action dated Dec. 9, 2020, issued in counterpart Taiwanese Patent Application No. 106114472 (w/ English machine translation; 10 pages).

Manavitehrani et al., "Biomedical Applications of Biodegradable Polyesters", Polymers, 2016, vol. 8, No. 20, pp. 1-32 (in English; cited in Taiwanese Office Action).

* cited by examiner

*Primary Examiner* — Doan T Phan
(74) *Attorney, Agent, or Firm* — Westerman, Hattori, Daniels and Adrian, LLP

(57) ABSTRACT

To provide a cosmetic which is environmentally friendly and is excellent in all of spreadability on application, adhesion, hand feeling properties and transparency. A cosmetic including aliphatic polyester-based resin particles, wherein the aliphatic polyester-based resin particles have a volume-average particle diameter of 2 to 30 μm, and a ratio of particles having a particle diameter of less than 1 μm is 15% by volume or less and a ratio of particles having a particle diameter of more than 30 μm is 6% by volume or less, is provided.

2 Claims, No Drawings

COSMETIC

TECHNICAL FIELD

The present invention relates to a cosmetic. More specifically, the present invention relates to a cosmetic which is environmentally friendly and exhibits satisfactory spreadability on application and adhesion, and is excellent in hand feeling properties (absence of foreign body sensation, softness, absence of squeaky sensation, slipperiness, smoothness) and transparency.

BACKGROUND ART

To improve spreadability on application, hand feeling properties (absence of foreign body sensation, softness, absence of squeaky sensation, slipperiness, smoothness) and uniformity, spherical fine particles having a particle diameter of 0.1 to 50 μm have hitherto been added to makeup cosmetics such as foundation, face powder, cheek, eye shadow and eyebrow, body cosmetics such as body powder and baby powder, and skin cosmetics such as lotion and milky lotion.

There have been known, for example, a cosmetic including spherical polyurethane fine powders having an average particle diameter of 30 μm or less (Patent Document 1); acrylic copolymer fine particles for cosmetic obtained by suspension polymerization of a monomer mixture including a (meth)acrylate monomer, an ethyl acrylate monomer and a polyfunctional vinyl monomer (Patent Document 2); a cosmetic including specific polyethylene-based resin spherical fine particles (Patent Document 3) and the like.

PRIOR ART DOCUMENT

Patent Document

Patent Document 1: JP 5-262622 A
Patent Document 2: JP 2001-151626 A
Patent Document 3: JP 2002-370920 A

DISCLOSURE OF THE INVENTION

Problems to be Solved by the Invention

However, polyurethane and an acrylic copolymer are excellent in spreadability on application and hand feeling properties because of excellent elasticity, but are inferior in transparency. Meanwhile, a polyethylene-based resin has insufficient heat resistance and it is difficult to achieve a balance of feeling in use (spreadability on application, hand feeling properties, transparency, etc.) according to the type of the cosmetic (e.g., cosmetic whose processing temperature is high), thus leaving room for further improvement. In recent years, in light of environmental problems on a global scale, there have been required to develop more environmentally friendly cosmetics.

Therefore, it is an object of the present invention to provide a cosmetic which is environmentally friendly and is excellent in all of spreadability on application, adhesion, hand feeling properties (absence of foreign body sensation, softness, absence of squeaky sensation, slipperiness, smoothness) and transparency.

Means for Solving the Problems

The present inventors have intensively studied so as to solve the above problems and found that a cosmetic including, as an essential component, aliphatic polyester-based resin particles having specific particle diameter and particle size distribution is environmentally friendly and is excellent in all of spreadability on application, adhesion, hand feeling properties and transparency, thus completing the present invention.

Namely, the present invention includes, for example, the following subject matters.

Item 1

A cosmetic including aliphatic polyester-based resin particles, wherein the aliphatic polyester-based resin particles have a volume-average particle diameter of 2 to 30 μm, and a ratio of particles having a particle diameter of less than 1 μm is 15% by volume or less and a ratio of particles having a particle diameter of more than 30 μm is 6% by volume or less.

Item 2

The cosmetic according to item 1, wherein a compressive strength at 10% displacement of the aliphatic polyester-based resin particles is 1 MPa or more.

Item 3

The cosmetic according to item 1 or 2, wherein the aliphatic polyester-based resin particles are resin particles comprising a glycol component and an aliphatic dicarboxylic acid component.

Item 4

The cosmetic according to item 1 or 2, wherein the aliphatic polyester-based resin particles are polylactic acid-based resin particles.

Item 5

The cosmetic according to any one of items 1 to 4, wherein an aliphatic polyester-based resin constituting the aliphatic polyester-based resin particles is a resin having biodegradability.

Effects of the Invention

The cosmetic according to the present invention is environmentally friendly and is excellent in all of spreadability on application, adhesion, hand feeling properties (absence of foreign body sensation, softness, absence of squeaky sensation, slipperiness, smoothness) and transparency.

DESCRIPTION OF THE EMBODIMENTS

The cosmetic according to the present invention is a cosmetic including (or comprising) aliphatic polyester-based resin particles as an essential component. The aliphatic polyester-based resin particles are particles made of an aliphatic polyester-based resin having a volume-average particle diameter of 2 to 30 μm, in which a ratio of particles having a particle diameter of less than 1 μm is 15% by volume or less and a ratio of particle having a particle diameter of more than 30 μm is 6% by volume or less.

Examples of the resin constituting the aliphatic polyester-based resin particles (aliphatic polyester-based resin) used in the cosmetic according to the present invention include resins including polylactic acid, a glycol component (constitutional unit derived from glycol or derivatives thereof) and an aliphatic dicarboxylic acid component (constitutional unit derived from an aliphatic dicarboxylic acid or derivatives thereof) (e.g., polyethylene succinate, polybutylene succinate, polyhexamethylene succinate, polyethylene adipate, polybutylene adipate, polyhexamethylene adipate, polyethylene oxalate, polybutylene oxalate, polyneopentyl oxalate, polyethylene sebacate, polybutylene sebacate, polyhexamethylene sebacate. etc.). These may be a polymer of only one kind of a monomer, or a copolymer of two or more kinds of monomers. Those including structures derived from these monomers as a main component may include other components, for example, structures derived from monomers such as an aromatic dicarboxylic acid and a polyfunctional monomer (e.g., a monomer having three or more hydroxyl groups, a monomer having three or more carboxylic acids). These resins can be inexpensively produced and a soil burial test widely reveals that the resins are biodegraded by microorganisms (having biodegradability). The cosmetic according to the present invention includes the aliphatic polyester-based resin particles and therefore exhibits moisture-retaining properties derived from hydrophilicity of the resin and also exhibits performances excellent in all of spreadability on application, adhesion, hand feeling properties (absence of foreign body sensation, softness, absence of squeaky sensation, slipperiness, smoothness) and transparency.

There is no particular limitation on the method for producing the aliphatic polyester-based resin particles, and a known method is used. For example, the following method is exemplified. First, an aliphatic polyester-based resin is melted at a temperature of a melting point or higher, together with a dispersant or an emulsifier, in a solvent in which the resin does not dissolve, for example, water, followed by stirring and further cooling to the temperature lower than the melting point to obtain a dispersion including spherical fine particles dispersed therein. Subsequently, the dispersion thus obtained is filtered, dried and optionally classified to obtain aliphatic polyester-based resin particles.

In the case of producing the aliphatic polyester-based resin particles, it is also possible to use a water-soluble polymer as the dispersant or emulsifier. Examples of the water-soluble polymer include a natural polymer or a synthetic polymer. Examples of the natural polymer include saccharides such as alginic acid, carboxymethyl cellulose, methyl cellulose, pullulan, dextran and xanthan gum; polysaccharides and chemically modified products thereof; and proteins such as gelatin. Examples of the synthetic polymer include an ethylene oxide/propylene oxide copolymer, polyvinyl alcohol, polyacrylic acid and salts thereof, polyacrylamide, polyvinylpyrrolidone, polyethylene oxide and the like. Of these polymers, an ethylene oxide/propylene oxide copolymer and polyvinyl alcohol are preferably used. These water-soluble polymers are usually used in a state of an aqueous solution after dissolving in water. In this case, the water-soluble polymer is preferably dissolved in the amount of 1 to 30 parts by mass, and particularly preferably 1 to 10 parts by mass, based on 100 parts by mass of water.

The ratio of the aliphatic polyester-based resin in the aliphatic polyester-based resin particles is preferably 90% by mass or more (e.g., 90 to 100% by mass), and more preferably 95% by mass or more.

The volume-average particle diameter of the aliphatic polyester-based resin particles is 2 to 30 μm, and the lower limit is preferably 4 μm (i.e., 4 μm or more) and the upper limit is preferably 20 μm (i.e., 20 μm or less). By adjusting the volume-average particle diameter to 2 μm or more, there is a tendency for the spreadability on application of the thus obtained cosmetic to be further improved. By adjusting the volume-average particle diameter to 30 μm or less, there is a tendency for the hand feeling properties on application (absence of foreign body sensation, softness, absence of squeaky sensation, slipperiness, smoothness) of the thus obtained cosmetic to be further improved. The volume-average particle diameter of the aliphatic polyester-based resin particles is measured using an electrical sensing particle size distribution analyzer (e.g., manufactured by Beckman Coulter, Inc. under the trade name of Coulter Multisizer) after dispersing 0.1 g of the aliphatic polyester-based resin particles in 10 g of water.

Regarding the aliphatic polyester-based resin particles, a ratio of particles having a particle diameter of less than 1 μm is 15% by volume or less, preferably 10% by volume or less, and more preferably 5% by volume or less. By adjusting the ratio to 15% by volume or less, there is a tendency for the squeaky sensation of the cosmetic to be absent and the slipperiness and smoothness of the cosmetic to be further improved.

Regarding the aliphatic polyester-based resin particles, a ratio of particles having a particle diameter of more than 30 μm is 6% by volume or less, preferably 3% by volume or less, and more preferably 1% by volume or less. By adjusting the ratio to 6% by volume or less, there is a tendency for the feeling in use of the cosmetic to be further improved (e.g., harshness is reduced).

The ratio of the aliphatic polyester-based resin particles (a ratio of particles having a particle diameter of less than 1 μm, a ratio of particles having a particle diameter of more than 30 μm) is calculated by reading from particle size distribution data measured by the above-mentioned procedure (electrical sensing particle size distribution analyzer).

The aliphatic polyester-based resin particles preferably have an average circularity of 90 or more. If the average circularity is 90 or more, the particle shape is not excessively distorted, thus making it possible to preferably obtain smooth feeling in use. The average circularity [average of (equivalent circle diameter/circumferential long diameter)] is measured using an image analysis particle size distribution analyzer (e.g., Microtrac PartAn SI, manufactured by MicrotracBEL Corp.).

The compressive strength at 10% displacement of the aliphatic polyester-based resin particles is preferably 1 MPa or more, and more preferably 3 to 30 MPa, in view of the feeling in use of the cosmetic. If the compressive strength at 10% displacement is 1 MPa or more, there is a tendency for the smoothness and spreadability on application of the cosmetic to be further improved. The compressive strength at 10% displacement is measured as a compressive strength at 10% displacement with respect to the particle shape by applying a load to particles, using Micro Compression Testing Machine (e.g., Micro Compression Testing Machine MCT-510, manufactured by Shimadzu Corporation). The compressive strength at 10% displacement of the aliphatic polyester-based resin particles can be controlled by appropriately selecting, for example, the kind, the crystallization state (crystallinity), the melt index (MI) and the like of the aliphatic polyester-based resin.

A durometer hardness (Shore D) of the aliphatic polyester-based resin particles is preferably 40 or more, and more preferably 50 to 120. If the durometer hardness (Shore D) is 40 or more, there is a tendency for the smoothness and spreadability on application of the cosmetic to be further improved. The durometer hardness (Shore D) is a value measured in accordance with JIS K7215. The durometer hardness (Shore D) of the aliphatic polyester-based resin particles can be controlled by appropriately selecting, for example, the kind, the crystallization state (crystallinity), the melt index (MI) and the like of the aliphatic polyester-based resin.

The content (blending ratio) of the aliphatic polyester-based resin particles in the cosmetic of the present invention is preferably 1% by mass or more, more preferably 3% by mass or more, and preferably 30% by mass or less, and more preferably 20% by mass or less, based on the total amount (100% by mass) of the cosmetic. In other words, the content is preferably 1 to 30% by mass, and more preferably 3 to 20% by mass. By adjusting the content (blending amount) of the aliphatic polyester-based resin particles to 1% by mass or more, there is a tendency for the spreadability on application and the hand feeling properties (absence of foreign body sensation, softness, absence of squeaky sensation, slipperiness, smoothness) of the cosmetic to be further improved. By adjusting the content to 30% by mass or less, it becomes more economically advantageous, and there is a tendency for the hand feeling properties on application of the cosmetic (absence of foreign body sensation, softness, absence of squeaky sensation, slipperiness, smoothness) to be further improved. In the cosmetic according to the present invention, the aliphatic polyester-based resin particles can be used alone, or in combination of two or more kinds thereof.

The cosmetic according to the present invention is not particularly limited as long as it includes the aliphatic polyester-based resin particles as a constitutional component and includes, for example, face powder, foundation, lipstick, cheek, eyeliner, mascara, eye shadow, base cream, milky lotion, skin lotion, cream and the like. The cosmetic according to the present invention may include various components, which are usually used in these cosmetics, in a conventional ratio. The cosmetic according to the present invention has moisture-retaining properties because of including the aliphatic polyester-based resin particles, and the particles may be coated or impregnated with other moisturizers according to application. Other moisturizers include, for example, polyhydric alcohols such as propylene glycol and glycerin; and natural polymers such as hyaluronic acid.

EXAMPLES

The present invention will be more specifically described by way of Examples, but the present invention is not limited to these Examples.

In the Examples, the volume-average particle diameter is a value obtained by performing the measurement using an electrical sensing particle size distribution analyzer (e.g., manufactured by Beckman Coulter, Inc. under the trade name of Coulter Multisizer) after dispersing 0.1 g of particles (e.g., aliphatic polyester-based resin particles) in 10 g of water, followed by the calculation of an average (the measurement was repeated three times).

In the Examples, the 10% displacement compressive strength was measured as a compressive strength at 10% displacement with respect to the particle shape by applying a load to particles, using Micro Compression Testing Machine (e.g., Micro Compression Testing Machine MCT-510, manufactured by Shimadzu Corporation).

In the Examples, the durometer hardness (Shore D) is a value measured in accordance with JIS K 7215.

Production Example 1

In a 300 mL pressure-resistant vessel equipped with a stirrer, 100 g of an aliphatic polyester-based resin (polybutylene succinate, durometer hardness (Shore D) of 60), 15 g of an ethylene oxide/propylene oxide copolymer having a weight-average molecular weight of 15,500 (manufactured by ADEKA Corporation under the trade name of Pluronic F108) and 135 g of water were charged, followed by sealing. Subsequently, while stirring at 500 rpm, the temperature was raised to 180° C. and the temperature inside the vessel was kept at 180° C. After stirring and cooling to 50° C., a water dispersion of the aliphatic polyester-based resin was taken out. In the above series of operations, the time, during which heat history of 100° C. or higher is applied to the aliphatic polyester-based resin, was controlled to about 30 minutes or less. The water dispersion thus obtained was filtered, dried and classified to obtain spherical particles of the aliphatic polyester-based resin. The aliphatic polyester-based resin (polybutylene succinate) particles thus obtained exhibited a volume-average particle diameter of 11.9 μm, a ratio of particles having a particle diameter of less than 1 μm of 2.0% by volume and a ratio of particles having a particle diameter of more than 30 μm of 0.4% by volume, a compressive strength at 10% displacement of 6 MPa (durometer hardness (Shore D) of 60) and a circularity of 96.

Production Example 2

In the same manner as in Production Example 1, except that an aliphatic polyester-based resin (polylactic acid, durometer hardness (Shore D) of 75) was used in place of the aliphatic polyester-based resin (polybutylene succinate) in Production Example 1, aliphatic polyester-based resin particles were obtained. The aliphatic polyester-based resin (polylactic acid) particles thus obtained exhibited a volume-average particle diameter of 8.6 μm, a ratio of particles having a particle diameter of less than 1 μm of 1.8% by volume and a ratio of particles having a particle diameter of more than 30 μm of 0.5% by volume, a compressive strength at 10% displacement of 20 MPa (durometer hardness (Shore D) of 73) and a circularity of 94.

Production Example 3

In the same manner as in Production Example 1, except that a polyolefin resin (low density polyethylene, durometer hardness (Shore D) of 43) was used in place of the aliphatic polyester-based resin (polybutylene succinate) in Production Example 1, spherical particles of the polyolefin resin (low density polyethylene) were obtained. The polyolefin resin (low density polyethylene) particles thus obtained exhibited a volume-average particle diameter of 11 μm, a ratio of particles having a particle diameter of less than 1 μm of 2.0% by volume and a ratio of particles having a particle diameter of more than 30 μm of 0.6% by volume, a compressive strength at 10% displacement of 3 MPa (durometer hardness (Shore D) of 43) and a circularity of 96.

Example 1

Powders prepared by blending the aliphatic polyester-based resin (polybutylene succinate) particles obtained in Production Example 1 and components other than an oil component (dimethylpolysiloxane, squalane, paraben) according to the formulation shown in Table 1 were mixed at 1,800 rpm for 20 minutes using Mechano-Mill (Model MM-10, manufactured by Okada Seiki Co., Ltd.), followed by the addition of the oil component and further mixing. This product filled an intermediate dish to obtain a solid foundation. In Example 1, "particles" in Table 1 indicate aliphatic polyester-based resin (polybutylene succinate) particles.

TABLE 1

Formulation of solid foundation

| Component | Ratio (% by weight) |
| --- | --- |
| Particles | 15.0 |
| Titanium oxide | 8.0 |
| Sericite | 45.2 |
| Talc | 10.0 |
| Titanated mica | 2.0 |
| Red iron oxide | 2.0 |
| Yellow iron oxide | 3.5 |
| Ultramarine | 1.0 |
| Aluminum stearate | 1.0 |
| Dimethylpolysiloxane | 5.0 |
| Squalane | 7.0 |
| Paraben | 0.2 |
| Perfume | 0.1 |

Example 2

In the same manner as in Example 1, except that the aliphatic polyester-based resin (polylactic acid) particles obtained in Production Example 2 were used, a solid foundation was obtained according to the formulation shown in Table 1. In Example 2, "particles" in Table 1 indicate aliphatic polyester-based resin (polylactic acid) particles.

Comparative Example 1

In the same manner as in Example 1, except that the polyolefin resin (low density polyethylene) particles obtained in Production Example 3 were used, a solid foundation was obtained according to the formulation shown in Table 1. In Comparative Example 1, "particles" in Table 1 indicate polyolefin resin (low density polyethylene) particles.

Example 3

A liquid A prepared by mixing while heating to 100° C. or higher and a liquid B prepared by mixing while heating to 100° C. or higher were gradually mixed, and then the aliphatic polyester-based resin (polybutylene succinate) particles obtained in Production Example 1 were mixed while heating under stirring, followed by cooling to 50° C. to obtain an emulsion according to the formulation shown in Table 2. In Example 3, "particles" in Table 2 indicate aliphatic polyester-based resin (polybutylene succinate) particles.

TABLE 2

Formulation of milky lotion

| | Component | Ratio (% by weight) |
| --- | --- | --- |
| Liquid A | Polyoxyethylenesorbitan monostearate | 1.2 |
| | Polyoxysorbitol tetraoleate | 1.3 |
| | Glyceryl monostearate | 1.3 |
| | Stearic acid | 0.5 |
| | Biphenyl alcohol | 1.0 |
| | Cetyl palmitate | 0.6 |
| | Squalane | 5.0 |
| | Cetyl 2-ethylhexanoate | 4.0 |
| | Polymethylsiloxane | 0.5 |
| Liquid B | 1,3-Butylene glycol | 10.0 |
| | Xanthan gum | 0.4 |
| | Purified water | 69.2 |
| | Particles | 5.0 |

Example 4

In the same manner as in Example 3, except that the aliphatic polyester-based resin (polylactic acid) particles obtained in Production Example 2 were used, a milky lotion was obtained according to the formulation shown in Table 2. In Example 4, "particles" in Table 2 indicate aliphatic polyester-based resin (polylactic acid) particles.

Comparative Example 2

In the same manner as in Example 3, except that the polyolefin resin (low density polyethylene) particles obtained in Production Example 3 were used, a milky lotion was obtained according to the formulation shown in Table 2. In Comparative Example 2, "particles" in Table 2 indicate polyolefin resin (low density polyethylene) particles.

Production Example 4

In a 300 mL pressure-resistant vessel equipped with a stirrer, 100 g of an aliphatic polyester-based resin (polybutylene succinate, durometer hardness (Shore D) of 60), 25 g of an ethylene oxide/propylene oxide copolymer having a weight-average molecular weight of 15,500 (manufactured by ADEKA Corporation under the trade name of Pluronic F108) and 125 g of water were charged, followed by sealing. Subsequently, while stirring at 750 rpm, the temperature was raised to 180° C. and the temperature inside the vessel was kept at 180° C. After stirring and cooling to 50° C., a water dispersion of the aliphatic polyester-based resin was taken out. In the above series of operations, the time, during which heat history of 100° C. or higher is applied to the aliphatic polyester-based resin, was controlled to about 30 minutes or less. The water dispersion thus obtained was filtered, dried and classified to obtain spherical particles of the aliphatic polyester-based resin. The aliphatic polyester resin (polybutylene succinate) particles thus obtained exhibited a volume-average particle diameter of 8.8 µm, a ratio of particles having a particle diameter of less than 1 µm of 12.0% by volume and a ratio of particles having a particle diameter of more than 30 µm of 0.2% by volume, a compressive strength at 10% displacement of 6 MPa (durometer hardness (Shore D) of 60) and a circularity of 97.

Production Example 5

In the same manner as in Production Example 4, except that an aliphatic polyester-based resin (polylactic acid, durometer hardness (Shore D) of 75) was used in place of the aliphatic polyester-based resin (polybutylene succinate) and the temperature inside the vessel was changed to 190° C. in Production Example 4, aliphatic polyester-based resin particles were obtained. The aliphatic polyester-based resin (polylactic acid) particles thus obtained exhibited a volume-average particle diameter of 5.6 µm, a ratio of particles having a particle diameter of less than 1 µm of 11.0% by volume and a ratio of particles having a particle diameter of more than 30 µM of 0.5% by volume, a compressive strength at 10% displacement of 20 MPa (durometer hardness (Shore D) of 73) and a circularity of 95.

Production Example 6

In a 300 mL pressure-resistant vessel equipped with a stirrer, 100 g of an aliphatic polyester-based resin (polybutylene succinate, durometer hardness (Shore D) of 60), 10 g of an ethylene oxide/propylene oxide copolymer having a weight-average molecular weight of 15,500 (manufactured by ADEKA Corporation under the trade name of Pluronic F108) and 140 g of water were charged, followed by sealing. Subsequently, while stirring at 500 rpm, the temperature was raised to 140° C. and the temperature inside the vessel was kept at 140° C. After stirring and cooling to 50° C., a water dispersion of the aliphatic polyester-based resin was taken out. In the above series of operations, the time, during which heat history of 100° C. or higher is applied to the aliphatic polyester-based resin, was controlled to about 30 minutes or less. The water dispersion thus obtained was filtered, dried and classified to obtain spherical particles of the aliphatic polyester-based resin. The aliphatic polyester resin (polybutylene succinate) particles thus obtained exhibited a volume-average particle diameter of 24.6 μm, a ratio of particles having a particle diameter of less than 1 μm of 1.1% by volume and a ratio of particles having a particle diameter of more than 30 μm of 4.5% by volume, a compressive strength at 10% displacement of 6 MPa (durometer hardness (Shore D) of 60) and a circularity of 95.

Production Example 7

In the same manner as in Production Example 6, except that an aliphatic polyester-based resin (polylactic acid, durometer hardness (Shore D) of 75) was used in place of the aliphatic polyester-based resin (polybutylene succinate) and the temperature inside the vessel was changed to 175° C. in Production Example 6, aliphatic polyester-based resin particles were obtained. The aliphatic polyester-based resin (polylactic acid) particles thus obtained exhibited a volume-average particle diameter of 22.4 μm, a ratio of particles having a particle diameter of less than 1 μm of 1.7% by volume and a ratio of particles having a particle diameter of more than 30 μm of 5.1% by volume, a compressive strength at 10% displacement of 20 MPa (durometer hardness (Shore D) of 73) and a circularity of 93.

Production Example 8

In a 300 mL pressure-resistant vessel equipped with a stirrer, 100 g of an aliphatic polyester-based resin (polybutylene succinate, durometer hardness (Shore D) of 60), 35 g of an ethylene oxide/propylene oxide copolymer having a weight-average molecular weight of 15,500 (manufactured by ADEKA Corporation under the trade name of Pluronic F108) and 115 g of water were charged, followed by sealing. Subsequently, while stirring at 1,000 rpm, the temperature was raised to 180° C. and the temperature inside the vessel was kept at 180° C. After stirring and cooling to 50° C., a water dispersion of the aliphatic polyester-based resin was taken out. In the above series of operations, the time, during which heat history of 100° C. or higher is applied to the aliphatic polyester-based resin, was controlled to about 30 minutes or less. The water dispersion thus obtained was filtered, dried and classified to obtain spherical particles of the aliphatic polyester-based resin. The aliphatic polyester resin (polybutylene succinate) particles thus obtained exhibited a volume-average particle diameter of 1.6 μm, a ratio of particles having a particle diameter of less than 1 μm of 19.3% by volume and a ratio of particles having a particle diameter of more than 30 μm of 0.0% by volume, a compressive strength at 10% displacement of 6 MPa (durometer hardness (Shore D) of 60) and a circularity of 97.

Production Example 9

In the same manner as in Production Example 8, except that an aliphatic polyester-based resin (polylactic acid, durometer hardness (Shore D) of 75) was used in place of the aliphatic polyester-based resin (polybutylene succinate), the rotational speed in the case of stirring was changed to 500 rpm and the temperature inside the vessel was changed to 190° C. in Production Example 8, aliphatic polyester-based resin particles were obtained. The aliphatic polyester resin (polylactic acid) particles thus obtained exhibited a volume-average particle diameter of 1.9 μm, a ratio of particles having a particle diameter of less than 1 μm of 20.0% by volume and a ratio of particles having a particle diameter of more than 30 μm of 0.0% by volume, a compressive strength at 10% displacement of 20 MPa (durometer hardness (Shore D) of 73) and a circularity of 96.

Production Example 10

In a 300 mL pressure-resistant vessel equipped with a stirrer, 100 g of an aliphatic polyester-based resin (polybutylene succinate, durometer hardness (Shore D) of 60), 5 g of an ethylene oxide/propylene oxide copolymer having a weight-average molecular weight of 15,500 (manufactured by ADEKA Corporation under the trade name of Pluronic F108) and 115 g of water were charged, followed by sealing. Subsequently, while stirring at 250 rpm, the temperature was raised to 140° C. and the temperature inside the vessel was kept at 140° C. After stirring and cooling to 50° C., a water dispersion of the aliphatic polyester-based resin was taken out. In the above series of operations, the time, during which heat history of 100° C. or higher is applied to the aliphatic polyester-based resin, was controlled to about 30 minutes or less. The water dispersion thus obtained was filtered, dried and classified to obtain spherical particles of the aliphatic polyester-based resin. The aliphatic polyester resin (polybutylene succinate) particles thus obtained exhibited a volume-average particle diameter of 28.9 μm, a ratio of particles having a particle diameter of less than 1 μm of 1.1% by volume and a ratio of particles having a particle diameter of more than 30 μm of 49.1% by volume, a compressive strength at 10% displacement of 6 MPa (durometer hardness (Shore D) of 60) and a circularity of 95.

Production Example 11

In the same manner as in Production Example 10, except that an aliphatic polyester-based resin (polylactic acid, durometer hardness (Shore D) of 75) was used in place of the aliphatic polyester-based resin (polybutylene succinate) and the temperature inside the vessel was changed to 175° C. in Production Example 10, aliphatic polyester-based resin particles were obtained. The aliphatic polyester resin (polylactic acid) particles thus obtained exhibited a volume-average particle diameter of 25.6 μm, a ratio of particles having a particle diameter of less than 1 μm of 0.1% by volume and a ratio of particles having a particle diameter of more than 30 μm of 32.0% by volume, a compressive strength at 10% displacement of 20 MPa (durometer hardness (Shore D) of 73) and a circularity of 93.

Example 5

In the same manner as in Example 1, except that the aliphatic polyester-based resin (polybutylene succinate) particles obtained in Production Example 4 were used, a solid foundation was obtained according to the formulation shown in Table 1. In Example 5, "particles" in Table 1 indicate aliphatic polyester-based resin (polybutylene succinate) particles.

Example 6

In the same manner as in Example 1, except that the aliphatic polyester-based resin (polylactic acid) particles obtained in Production Example 5 were used, a solid foundation was obtained according to the formulation shown in Table 1. In Example 6, "particles" in Table 1 indicate aliphatic polyester-based resin (polylactic acid) particles.

Example 7

In the same manner as in Example 1, except that the aliphatic polyester-based resin (polybutylene succinate) particles obtained in Production Example 6 were used, a solid foundation was obtained according to the formulation shown in Table 1. In Example 7, "particles" in Table 1 indicate aliphatic polyester-based resin (polybutylene succinate) particles.

Example 8

In the same manner as in Example 1, except that the aliphatic polyester-based resin (polylactic acid) particles obtained in Production Example 7 were used, a solid foundation was obtained according to the formulation shown in Table 1. In Example 8, "particles" in Table 1 indicate aliphatic polyester-based resin (polylactic acid) particles.

Example 9

In the same manner as in Example 3, except that the aliphatic polyester-based resin (polybutylene succinate) particles obtained in Production Example 4 were used, a milky lotion was obtained according to the formulation shown in Table 2. In Example 9, "particles" in Table 2 indicate aliphatic polyester-based resin (polybutylene succinate) particles.

Example 10

In the same manner as in Example 3, except that the aliphatic polyester-based resin (polylactic acid) particles obtained in Production Example 5 were used, a milky lotion was obtained according to the formulation shown in Table 2. In Example 10, "particles" in Table 2 indicate aliphatic polyester-based resin (polylactic acid) particles.

Example 11

In the same manner as in Example 3, except that the aliphatic polyester-based resin (polybutylene succinate) particles obtained in Production Example 6 were used, a milky lotion was obtained according to the formulation shown in Table 2. In Example 11, "particles" in Table 2 indicate aliphatic polyester-based resin (polybutylene succinate) particles.

Example 12

In the same manner as in Example 3, except that the aliphatic polyester-based resin (polylactic acid) particles obtained in Production Example 7 were used, a milky lotion was obtained according to the formulation shown in Table 2. In Example 12, "particles" in Table 2 indicate aliphatic polyester-based resin (polylactic acid) particles.

Production Example 12

In a 300 mL pressure-resistant vessel equipped with a stirrer, 100 g of an aliphatic polyester-based resin (polybutylene succinate, durometer hardness (Shore D) of 60), 35 g of polyvinyl alcohol having a saponification degree of 78 to 81 and a polymerization degree of 2,000 (trade name of KURARAY CO., LTD.: PVA420) and 115 g of water were charged, followed by sealing. Subsequently, while stirring at 500 rpm, the temperature was raised to 180° C. and the temperature inside the vessel was kept at 180° C. After stirring and cooling to 50° C., a water dispersion of the aliphatic polyester-based resin was taken out. In the above series of operations, the time, during which heat history of 100° C. or higher is applied to the aliphatic polyester-based resin, was controlled to about 30 minutes or less. The water dispersion thus obtained was filtered, dried and classified to obtain spherical particles of the aliphatic polyester-based resin. The aliphatic polyester-based resin (polybutylene succinate) particles thus obtained exhibited a volume-average particle diameter of 15.5 μm, a ratio of particles having a particle diameter of less than 1 μm of 1.0% by volume and a ratio of particles having a particle diameter of more than 30 μm of 0.2% by volume, a compressive strength at 10% displacement of 6 MPa (durometer hardness (Shore D) of 60) and a circularity of 96.

Example 13

In the same manner as in Example 1, except that the aliphatic polyester-based resin (polybutylene succinate) particles obtained in Production Example 12 were used, a solid foundation was obtained according to the formulation shown in Table 1. In Example 13, "particles" in Table 1 indicate aliphatic polyester-based resin (polybutylene succinate) particles.

Example 14

In the same manner as in Example 3, except that the aliphatic polyester-based resin (polybutylene succinate) particles obtained in Production Example 12 were used, a milky lotion was obtained according to the formulation shown in Table 2. In Example 14, "particles" in Table 2 indicate aliphatic polyester-based resin (polybutylene succinate) particles.

Comparative Example 3

In the same manner as in Example 1, except that the aliphatic polyester-based resin (polybutylene succinate) particles obtained in Production Example 8 were used, a solid foundation was obtained according to the formulation shown in Table 1. In Comparative Example 3, "particles" in Table 1 indicate aliphatic polyester-based resin (polybutylene succinate) particles.

Comparative Example 4

In the same manner as in Example 1, except that the aliphatic polyester-based resin (polylactic acid) particles obtained in Production Example 9 were used, a solid foundation was obtained according to the formulation shown in Table 1. In Comparative Example 4, "particles" in Table 1 indicate aliphatic polyester-based resin (polylactic acid) particles.

Comparative Example 5

In the same manner as in Example 1, except that the aliphatic polyester-based resin (polybutylene succinate) particles obtained in Production Example 10 were used, a solid foundation was obtained according to the formulation shown in Table 1. In Comparative Example 5, "particles" in Table 1 indicate aliphatic polyester-based resin (polybutylene succinate) particles.

Comparative Example 6

In the same manner as in Example 1, except that the aliphatic polyester-based resin (polylactic acid) particles obtained in Production Example 11 were used, a solid foundation was obtained according to the formulation shown in Table 1. In Comparative Example 6, "particles" in Table 1 indicate aliphatic polyester-based resin (polylactic acid) particles.

Comparative Example 7

In the same manner as in Example 3, except that the aliphatic polyester-based resin (polybutylene succinate) particles obtained in Production Example 8 were used, a milky lotion was obtained according to the formulation shown in Table 2. In Comparative Example 7, "particles" in Table 2 indicate aliphatic polyester-based resin (polybutylene succinate) particles.

Comparative Example 8

In the same manner as in Example 3, except that the aliphatic polyester-based resin (polylactic acid) particles obtained in Production Example 9 were used, a milky lotion was obtained according to the formulation shown in Table 2. In Comparative Example 8, "particles" in Table 2 indicate aliphatic polyester-based resin (polylactic acid) particles.

Comparative Example 9

In the same manner as in Example 3, except that the aliphatic polyester-based resin (polybutylene succinate) particles obtained in Production Example 10 were used, a milky lotion was obtained according to the formulation shown in Table 2. In Comparative Example 9, "particles" in Table 2 indicate aliphatic polyester-based resin (polybutylene succinate) particles.

Comparative Example 10

In the same manner as in Example 3, except that the aliphatic polyester-based resin (polylactic acid) particles obtained in Production Example 11 were used, a milky lotion was obtained according to the formulation shown in Table 2. In Comparative Example 10, "particles" in Table 2 indicate aliphatic polyester-based resin (polylactic acid) particles.

Evaluation

The feeling in use of the solid foundations and the milky lotions obtained in the respective Examples and Comparative Examples was evaluated by ten evaluation panelists. Specifically, each item of spreadability on application, adhesion, hand feeling properties (foreign body sensation, softness) and transparency was evaluated as the feeling in use by the following four-rank evaluation criteria.

Evaluation Criteria

⊚: Excellent (10 persons felt good)
○: Good (8 to 9 persons felt good)
Δ: Ordinary (6 to 7 persons felt good)
x: Poor (5 or less persons felt good)

TABLE 3

|  |  | Spherical particles | Spreadability | Adhesion | Foreign body sensation | Softness | Transparency |
|---|---|---|---|---|---|---|---|
| Solid foundation | Example 1 | Production Example 1 | ⊚ | ○ | ⊚ | ⊚ | ○ |
|  | Example 2 | Production Example 2 | ⊚ | ⊚ | ⊚ | ○ | ⊚ |
|  | Example 5 | Production Example 4 | Δ | ○ | ⊚ | ○ | ○ |
|  | Example 6 | Production Example 5 | Δ | ○ | ⊚ | Δ | ○ |
|  | Example 7 | Production Example 6 | ○ | Δ | ○ | ○ | ○ |
|  | Example 8 | Production Example 7 | ○ | ○ | ○ | ○ | ○ |
|  | Example 13 | Production Example 12 | ⊚ | ○ | ⊚ | ⊚ | ○ |
|  | Comparative Example 1 | Production Example 3 | Δ | X | Δ | Δ | Δ |
|  | Comparative Example 3 | Production Example 8 | X | Δ | ⊚ | Δ | ○ |
|  | Comparative Example 4 | Production Example 9 | X | Δ | ⊚ | Δ | ○ |
|  | Comparative Example 5 | Production Example 10 | Δ | X | X | X | Δ |
|  | Comparative Example 6 | Production Example 11 | Δ | X | X | X | Δ |
| Milky lotion | Example 3 | Production Example 1 | ○ | ⊚ | ⊚ | ○ | ○ |
|  | Example 4 | Production Example 2 | ⊚ | ⊚ | ⊚ | ○ | ○ |
|  | Example 9 | Production Example 4 | ○ | ○ | ⊚ | ○ | ○ |
|  | Example 10 | Production Example 5 | ○ | ○ | ⊚ | Δ | ○ |
|  | Example 11 | Production Example 6 | ○ | Δ | ○ | ○ | ○ |

TABLE 3-continued

| | Spherical particles | Spreadability | Adhesion | Foreign body sensation | Softness | Transparency |
|---|---|---|---|---|---|---|
| Example 12 | Production Example 7 | ○ | ○ | ○ | ○ | ○ |
| Example 14 | Production Example 12 | ○ | ⊚ | ⊚ | ○ | ○ |
| Comparative Example 2 | Production Example 3 | Δ | Δ | X | Δ | X |
| Comparative Example 7 | Production Example 8 | X | ○ | ⊚ | Δ | ○ |
| Comparative Example 8 | Production Example 9 | X | Δ | ⊚ | Δ | ○ |
| Comparative Example 9 | Production Example 10 | Δ | X | X | X | X |
| Comparative Example 10 | Production Example 11 | Δ | X | X | X | X |

As is apparent from Table 3, the cosmetics including the aliphatic polyester-based resin particles of the respective Examples are not rated poor (x) with respect to spreadability on application, adhesion, hand feeling properties (foreign body sensation, softness) and transparency, and are excellent in all of these properties. Meanwhile, the cosmetics of the Comparative Examples were not excellent in all of spreadability on application, hand feeling properties (foreign body sensation), transparency and hand feeling properties (softness) (i.e., the cosmetics were rated as poor (x) with respect to any one of some properties).

INDUSTRIAL APPLICABILITY

The cosmetic of the present invention can be preferably used as cosmetics, for example, foundation, lipstick, cheek, eyeliner, eye shadow, eyebrow, mascara, face powder, dusting powder, cream, lotion, pre-shave lotion, after-shave lotion, milky lotion, skin lotion, deodorant and the like.

The invention claimed is:

1. A cosmetic comprising aliphatic polyester-based resin particles, wherein the aliphatic polyester-based resin particles are resin particles consisting of polybutylene succinate and a polymer dispersant, wherein the aliphatic polyester-based resin particles have a volume-average particle diameter of 2 to 30 μm, a shore D hardness of 50-120, and a ratio of particles having a particle diameter of less than 1 μm is 15% by volume or less and a ratio of particles having a particle diameter of more than 30 μm is 6% by volume or less, and
    wherein a compressive strength at 10% displacement of the aliphatic polyester-based resin particles is 1 MPa or more.

2. A cosmetic comprising aliphatic polyester-based resin particles,
    wherein the aliphatic polyester-based resin particles consist of polybutylene succinate, and
    wherein the aliphatic polyester-based resin particles have a volume-average particle diameter of 2 to 30 μm, a shore D hardness of 50-120, and a ratio of particles having a particle diameter of less than 1 μm is 15% by volume or less and a ratio of particles having a particle diameter of more than 30 μm is 6% by volume or less.

* * * * *